United States Patent [19]

Miwa

[11] Patent Number: 5,696,573

[45] Date of Patent: Dec. 9, 1997

[54] OPHTHALMIC APPARATUS

[75] Inventor: Tetsuyuki Miwa, Nukata-gun, Japan

[73] Assignee: Nidek Co., Ltd., Aichi, Japan

[21] Appl. No.: 602,297

[22] Filed: Feb. 16, 1996

[30] Foreign Application Priority Data

Feb. 28, 1995 [JP] Japan ............................ 7-68636

[51] Int. Cl.$^6$ .................. A61B 3/14; A61B 3/10
[52] U.S. Cl. ............................. 351/208; 351/205
[58] Field of Search .......................... 351/208, 206,
351/205, 211, 212, 221, 245, 246, 247, 200

[56] References Cited

U.S. PATENT DOCUMENTS

| | | |
|---|---|---|
| 5,279,300 | 1/1994 | Miwa et al. |
| 5,406,076 | 4/1995 | Mimura et al. |
| 5,532,769 | 7/1996 | Miwa et al. ............ 351/208 |

FOREIGN PATENT DOCUMENTS

| | | |
|---|---|---|
| 5-176895 | 7/1993 | Japan. |
| 7-265268 | 10/1995 | Japan. |

*Primary Examiner*—Hung X. Dang
*Attorney, Agent, or Firm*—Oliff & Berridge

[57] ABSTRACT

An ophthalmic apparatus including a measuring device for measuring an eye to be examined comprises a moving device for moving the measuring device with respect to the eye to be examined, a detecting device for detecting an alignment state between the measuring device and the eye, a control device for controlling operation of the moving device on the basis of detection results of the detecting device, a judging device for judging the alignment state on the basis of the detection results of the detecting device, a trigger signal generating device for generating trigger signals to make the measuring device start measurement based on judgement results of the judging device, and a stopping device for stopping operation of the moving device for a first predetermined time after completion of measurement by the measuring device.

8 Claims, 5 Drawing Sheets

1
OPHTHALMIC APPARATUS

BACKGROUND OF THE INVENTION

1. Field of the Invention

The present invention relates to an ophthalmic apparatus capable of automatically judging the propriety of an alignment slate between the apparatus and an eye to be examined.

2. Description of Related Art

Ophthalmic apparatuses in use for examination and measurement of eyes are required aligning to have a predetermined positional relation with respect to an eye to be measured.

As a noncontact tonometer which needs strictly high alignment precision, proposed is an apparatus provided with a detecting mechanism to detect an alignment state of the apparatus, which moves a measuring part thereof with respect to an eye to be examined thereby to perform alignment adjustment.

The applicant of the present invention also proposed "Ophthalmologic Alignment Devices" in U.S. Ser. No. 08/406,403, which performs automatic alignment.

In this apparatus, an alignment index light is projected to a cornea of an eye to be examined and the corneal reflection light is detected by a light detecting element, then a measuring system is driven to move on the basis of detection results to perform alignment. After completion of alignment, a signal to start measurement is generated. Thus measurement is automatically started.

The above-mentioned apparatus, however, involves a problem that a measurement starting condition may be fulfilled even under a state where an eye to be examined is not sufficiently fixed due to the slight movement of the eye and is not fully opened, resulting in the eyelashes blocking off the alignment index light. Especially, the probability is high that, in such an apparatus which performs automatically alignment, measurement starts sequentially, even if an eye to be examined is not in a fully opened state.

SUMMARY OF THE INVENTION

The present invention has been made in view of the above circumstances and has an object to overcome the above problems and to provide an ophthalmic apparatus capable of preventing measurement from starting when an eye to be examined is not opened sufficiently, thereby to obtain measurement results with high reliability.

Additional objects and advantages of the invention will be set forth in part in the description which follows and in part will be obvious from the description, or may be learned by practice of the invention. The objects and advantages of the invention may be realized and attained by means of the instrumentalities and combinations particularly pointed out in the appended claims.

To achieve the objects and in accordance with the purpose of the invention, as embodied and broadly described herein, an ophthalmic apparatus of this invention including measuring means for measuring an eye to be examined, the apparatus comprising moving means for moving the measuring means with respect to the eye to be examined, detecting means for detecting an alignment state between the measuring means and the eye to be examined, control means for controlling operation of the moving means on the basis of detection results of the detecting means, judging means for judging the alignment state on the basis of the detection results of the detecting means, trigger signal generating means for generating trigger signals to make the measuring means start measurement based on judgement results of the judging means, and stopping means for stopping operation of the moving means for a first predetermined time after completion of measurement by the measuring means.

According to the present invention, it is possible to provide the examinee the time to fully open and fix the eye to be examined, and also to avoid sequence measurement in an insufficient alignment state, which results in obtaining measurement results with high reliability.

BRIEF DESCRIPTION OF THE DRAWINGS

The accompanying drawings, which are incorporated in and constitute a part of this specification illustrate embodiments of the invention and, together with the description, serve to explain the objects, advantages and principles of the invention. In the drawings.

DETAILED DESCRIPTION OF THE PREFERRED EMBODIMENTS

A detailed description of preferred embodiments of an ophthalmic apparatus embodying the present invention will now be given referring to the accompanying drawings.

Figure 1:
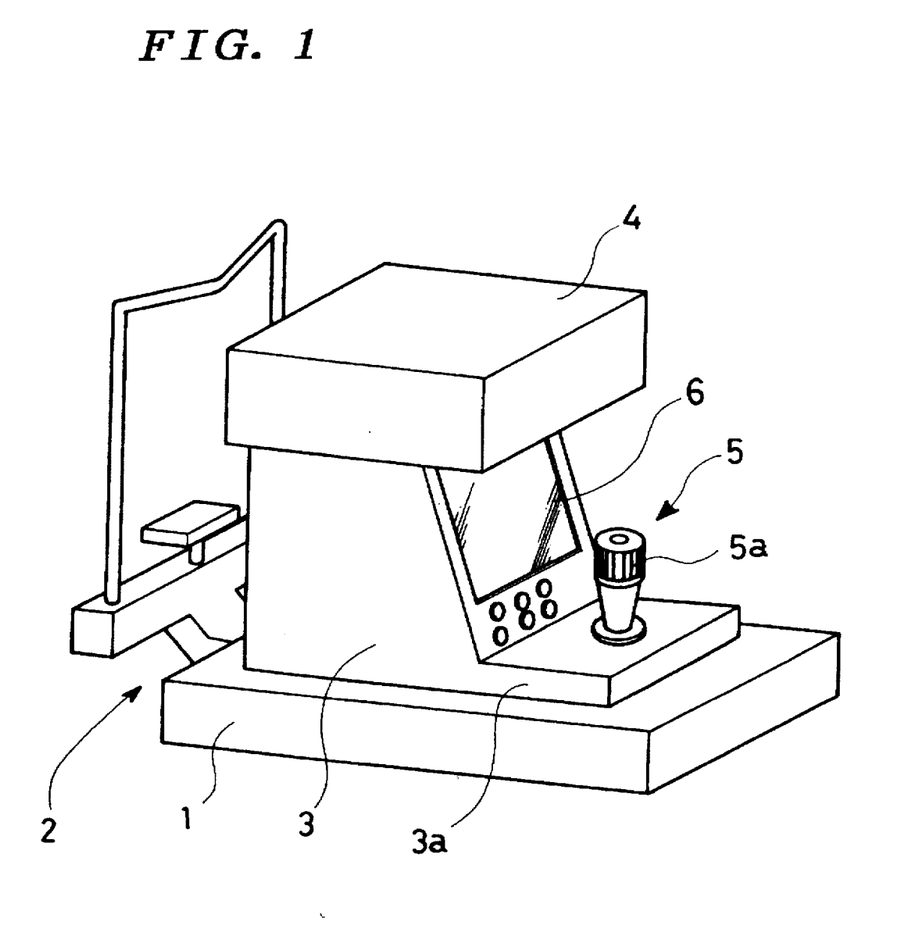
FIG. 1 is a schematic view of an outer appearance of a noncontact tonometer in the first embodiment.

FIG. 1 shows an outer appearance simplified of a noncontact tonometer in the first embodiment.

A base 1 is provided with a chin rest 2 for supporting an eye to be examined at a predetermined position. On the base 1, a main body 3 is movably mounted. The main body 3 and a measuring part 4 containing a measuring system 4A and an optical system (mentioned later) can be moved on the base 1 by the manual operation of a joy stick 5, specifically, the main body 3 can be moved forward and backward and to the right and left on a horizontal plane on the base 1 and the measuring part 4 vertically with respect to the main body 3.

Figure 2:
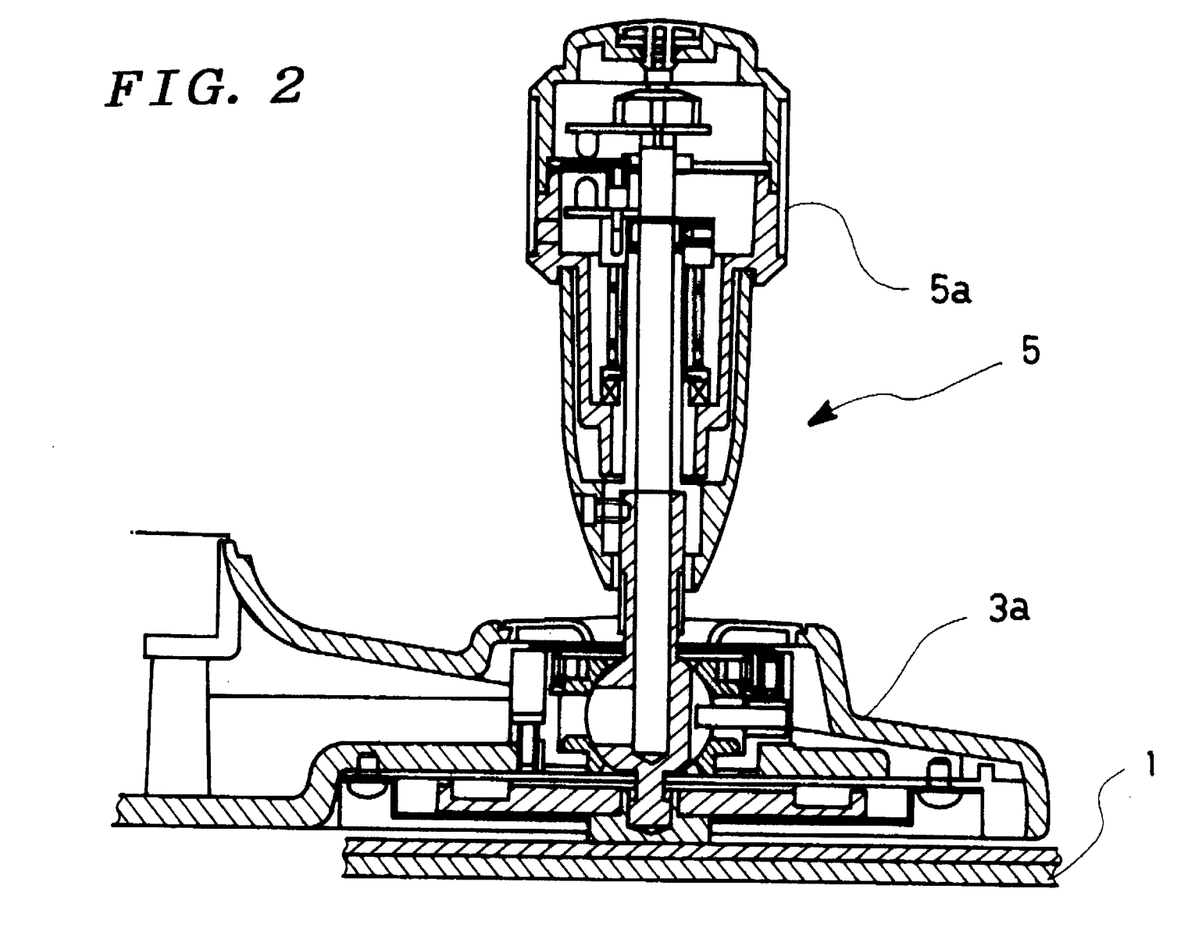
FIG. 2 is a sectional view of a joy stick of the apparatus of the invention.

FIG. 2 shows a sectional view of the joy stick 5. The movement of the main body 3 horizontally on the base 1 can be effected by a mechanism of the joy stick 5 constructed of a spherical portion and a lower end portion formed on a lower portion of a shaft, a sliding board to be swung by the lower end portion, a friction board attached on the base 1 so as to be in contact with the sliding board and a ball bearing arranged inside of a housing 3a formed integratedly in the main body 3. Through these elements fine horizontal movement of the main body 3 is realized.

The vertical movement of the measuring part 4 with respect to the main body 3 is effected through other elements of the joy stick 5, namely, a rotating knob 5a provided on an upper outer periphery of the joy stick 5, a slit plate which rotates simultaneously with the rotating knob 5a, a light source and a light receiving element which are arranged on the opposite sides of the slit plate. In such a joy stick 5, a direction and an amount of rotation of the rotating knob 5b are detected on the basis of signals of the light receiving element and, based on the detected results, a motor whereby the measuring part 4 is moved vertically is driven and controlled. The mechanism of the joy stick 5 is described in detail in U.S. Pat. No. 5,406,076 suggested by the applicant of the present invention, the title of which is Joy Stick Mechanism for Ophthalmic Apparatus. Therefore its more detail explanation is to be referred to that Patent.

For automatic alignment, additionally, the measuring part 4 can be moved 5 mm from a reference position to the right and left respectively, 20 mm forward and 30 mm vertically.

A monitor television 6 is provided in the examiner's side of the main body 3, which displays an image of the anterior part of an eye to be examined and information to be informed to the examiner.

Figure 3:
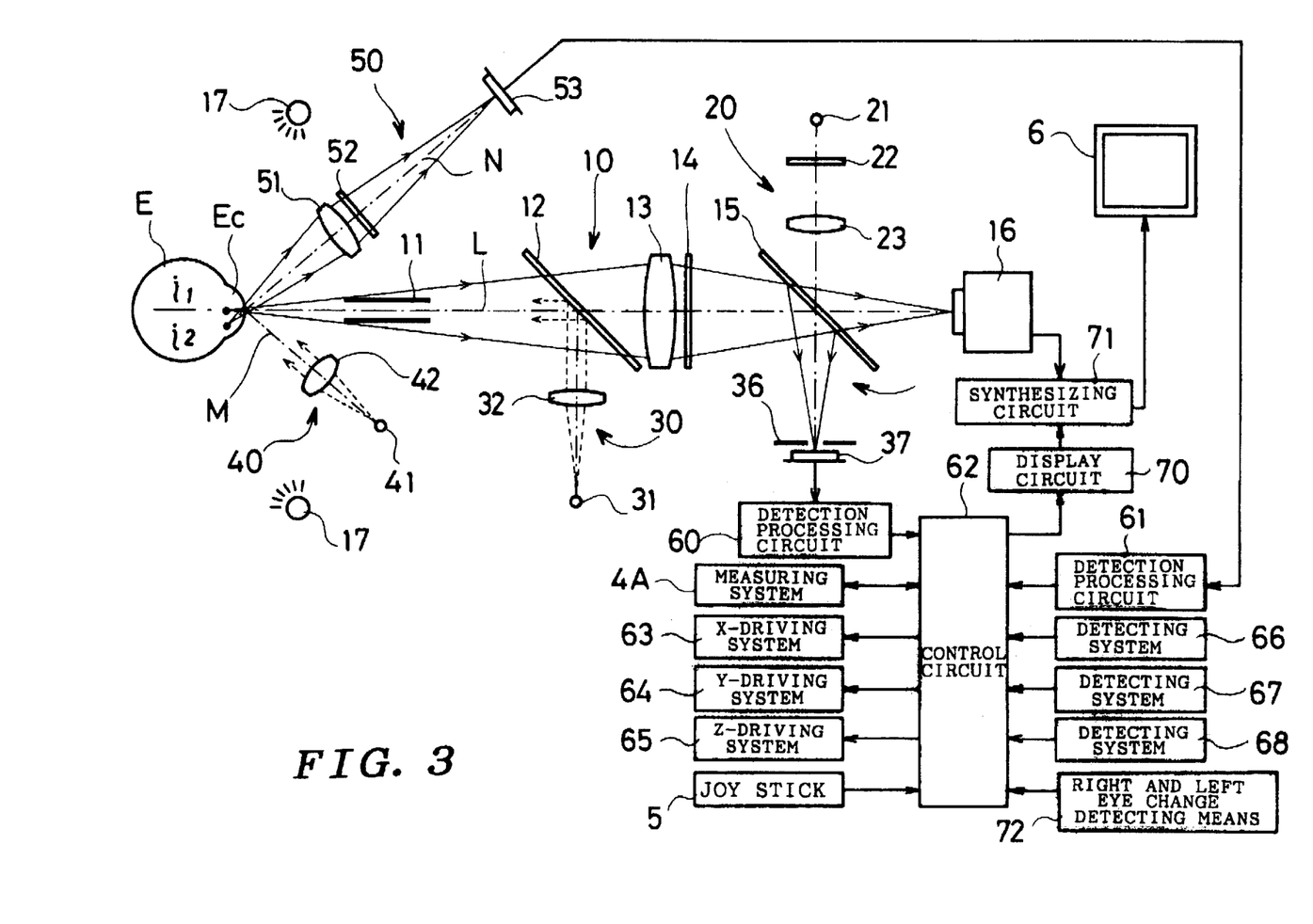
FIG. 3 is a schematic diagram for showing an alignment optical system and a control system of the apparatus.

FIG. 3 shows a main interior structure of the apparatus in the first embodiment. An alignment optical system and a control system will be hereinafter explained in order.

A noncontact tonometer is an apparatus to measure intraocular pressure of an eye, by injecting a compressed air to a cornea of the eye to be examined thereby to deform it, detecting a deformation of the cornea into a predetermined state and directly or indirectly the air pressure when the cornea is deformed into a predetermined form. In this manner the noncontact tonometer measures the intraocular pressure of the eye on the basis of the detected air pressure value. This measuring mechanism itself has little relation to the present invention, so that the explanation described in U.S. Pat. No. 5,279,300 suggested by the present applicant, the title of which is Noncontact Type Tonometer, is hereby incorporated by reference.

Alignment Optical System

The alignment optical system of the apparatus includes an observing optical system, a reticle projecting optical system, a front index projecting optical system, a front index detecting optical system, a distance index projecting optical system and a distance index detecting optical system, which will be hereinafter described respectively.

(Observing optical system)

An observing optical system 10 has an optical axis denoted by L. On the optical path of the observing optical system 10, located is a nozzle 11 for injecting air fluid to deform a cornea of an eye E to be examined, an axis of which coincides with the optical axis L. On the optical axis L, coaxially arranged are a half mirror 12, an objective lens 13, a filter 14, a half mirror 15 and a TV camera 16. The filter 14 has the property of allowing the luminous flux having a wavelength of light from the front index projecting optical system, which is mentioned later, to pass, while the luminous flux having a wavelength of light from the distance index projecting optical system not to pass, so that it prevents unnecessary noise light from reaching the TV camera 16 and the light receiving element of the front index detecting optical system.

An illumination light source 17 (two elements are shown in this embodiment) emits near-infrared light for observation of an eye E. The luminous flux from the illumination light source 17 illuminates the eye E and the reflected light is condensed by the objective lens 13 and directed onto an imaging plane of the TV camera 16 through the half mirror 12, the filter 14 and the half mirror 15, thus an image of the anterior part of the eye E is displayed on the TV monitor 6.

(Reticle projecting optical system)

A reticle projecting optical system 20 comprises a light source 21, a reticle plate 22 on which a circular mark is provided and a projection lens 23. The light from the light source 21 illuminates the reticle plate 22, passes through the projection lens 23 and is reflected by the half mirror 15, thereby producing an image of a circular reticle of the reticle plate 22 on the imaging plane of the TV camera 16. The reticle image is displayed on the TV monitor 6 while being superimposed on the image of the anterior part of the eye E.

(Front index projecting optical System)

A front index projecting optical system 30 is constituted of a light source 31 and a projection lens 32. The light source 31 is constituted of a near infrared ray LED and the like, which emits light having a wavelength near to that of the illumination light source 17. To the output of the light source 31, applied is modulation with a predetermined frequency in order to prevent the luminous flux from the illumination light source 17 from becoming noise to a front index detecting optical system (mentioned later) for detecting the light from the light source 31.

The light from the light source 31 is allowed to become a luminous flux formed of parallel rays by the projection lens 32, and is reflected to the half mirror 12 and passed through the inside of the nozzle 11 and others to irradiate the cornea Ec. The luminous flux is specularly reflected on the cornea Ec and forms an index i1 which is a virtual image of the light source 31 in the eye E. The luminous flux of the index i1 is directed back along the optical axis L of the observing optical system to the TV camera 16 and then forms an index image on the imaging plane of the TV camera 16.

(Front index detecting optical system)

A front index detecting optical system 35 is constituted of a field stop 36, a two dimensional position detecting element 37, the objective lens 13, the filter 14 and the half mirror 15. The components 13, 14 and 15 are used in common with the observing optical system.

The field stop 36 has a diameter designed so as to prevent unnecessary light from entering the detecting element 37 while allowing the luminous flux of an image of the index i1 to be incident on the detecting element 37 when the index image is in a substantially proper position with respect to the reticle image on the TV camera 16. As the two dimensional position detecting element 37, various sensors such as a charge coupled device (CCD), a position sensor detector (PSD) and others can be used selectively. Instead of the two dimensional position detecting element, two- or four-divided type of photo-detecting elements may be used.

After specular reflection due to the cornea Ec, the luminous flux of the front index is directed by the half mirror 15 to the front index detecting optical system 35, wherein it passes through the field stop 36 and reaches the light receiving element 37. This light receiving element 37 detects the position of the eye E in a vertical direction and in a right and left direction with respect to the measuring optical axis (an observing optical axis L) based on the two-dimensional position of the luminous flux of index i1 incident on a detection surface of the detecting element 37.

(Distance index projecting optical system)

A distance index projecting optical system 40 has an optical axis denoted by M. The optical axis M is so designed as to incline relating to the optical axis L of the observing optical system 30 and also to intersect the same at a position apart from the nozzle 11 by a predetermined working distance. As an intersecting angle of the optical axis M to the optical axis L, it is preferable to select it in the angle range from 20° to 40°. On the optical axis M, arranged are a light source 41 for emitting a light beam having a wavelength different from that of the light source 31, such as a LED and the like, and a projection lens 42.

The light emitted from the light source 41 passes through the projection lens 42, thereby becoming a luminous flux formed of parallel rays, and is directed along the optical axis M to irradiate the cornea Ec. The luminous flux is specularly reflected on the cornea Ec and forms an index i2 which is a virtual image of the light source 41.

(Distance index detecting optical system)

A distance index detecting optical system 50 has an optical axis denoted by N. The optical axis N and the optical axis M are symmetrical with respect to the optical axis L, so that the optical axis N intersects the optical axis M on the optical axis L. On the optical axis N, coaxially provided are a light receiving lens 51, a filter 52 and the one-dimensional position detecting element 53. The filter 52 has the property of allowing the light having a wavelength of light from the light source 41 to pass and the light having wavelengths of light from the illumination light source 17 and the light source 31 of the front index projecting optical system 30 respectively not to pass, thereby to prevent light beams of the index i1 and the illumination light source 17 from being incident on the one-dimensional detecting element 53 and becoming noise to the distance index detecting optical system 50.

The corneal reflection luminous flux of the light source 41, forming an index image i2, is passed through the light receiving lens 51 and the filter 52 and is incident on the one-dimensional position detecting element 53. When the eye E moves in a direction along the optical axis L, namely, in a forward and backward direction, the image of the index i2 formed by the light receiving lens 51 on the one-dimensional detecting element 53 is simultaneously moved on a detection plane of the one-dimensional detecting element 53 in its detection direction. On the basis of the displacement amount of the index image on the one-dimensional detecting element 53, the position of the eye E with respect to the apparatus in a forward and backward direction is detected.

A cylindrical lens having a generatrix in the detection direction may be provided in the front of the one-dimensional detecting element 53.

Control System

A control system of the apparatus in the embodiment will be next described.

Signals outputted from the two-dimensional position detecting element 37 and the one-dimensional position detecting element 53 are processed in detection processing circuits 60 and 61 respectively and inputted to a control circuit 62. The control circuit 62 makes a known process on the signals to obtain the displacement amount of the eye E from a proper position in a vertical, a right and left, and a forward and backward directions.

The control circuit 62 is also connected to an X-driving system 63 for moving the measuring part 4 with respect to the main body 3 in a right and left direction, namely, an X-direction, a Y-driving system 64 for moving the measuring part 4 in a vertical direction, namely, a Y-direction, and a Z-driving system 65 for moving the measuring part 4 in a forward and backward direction, namely, a Z-direction, respectively.

Each of the driving systems 63, 64 and 65 includes a motor and a motor driving circuit and is to be driven based on the signals corresponding to the displacement information in each direction, which is calculated by the control circuit 62, thereby realizing automatic alignment function. Automatic alignment in the present embodiment is designed to make a three directions drive, i.e., in a right and left, vertical and forward and backward directions. Alignment accuracy in a forward and backward direction is not so strictly required to noncontact tonometers as in a right and left, vertical directions. And in consideration of preventing the nozzle 11 from contacting the eye E, the Z-direction driving system 65 may be omitted and alignment in a Z-direction may be performed only by operating the joy stick 5. It is possible to add modifications and variations to the apparatus, for example, designating the direction of manual alignment by the joy stick 5.

To the control circuit 62, connected are a detecting system 66 for detecting a limitation of movement in an X-direction and a center position in a right and left direction, a detecting system 67 for detecting a limitation of movement in a Y-direction and a detecting system 68 for detecting a limitation of movement of a Z-direction. Each detecting system is constructed of a sensor of transmission type and a shading plate or a microswitch and the like.

Numeral 70 is a character displaying circuit for producing figures, letters and the like to inform an alignment state and other information to the examiner. Numeral 71 is a synthesizing circuit for synthesizing picture signals transmitted from the TV camera 16 and signals from the character displaying circuit 70, thereby displaying them synthesized on the TV monitor 6.

Figure 4:
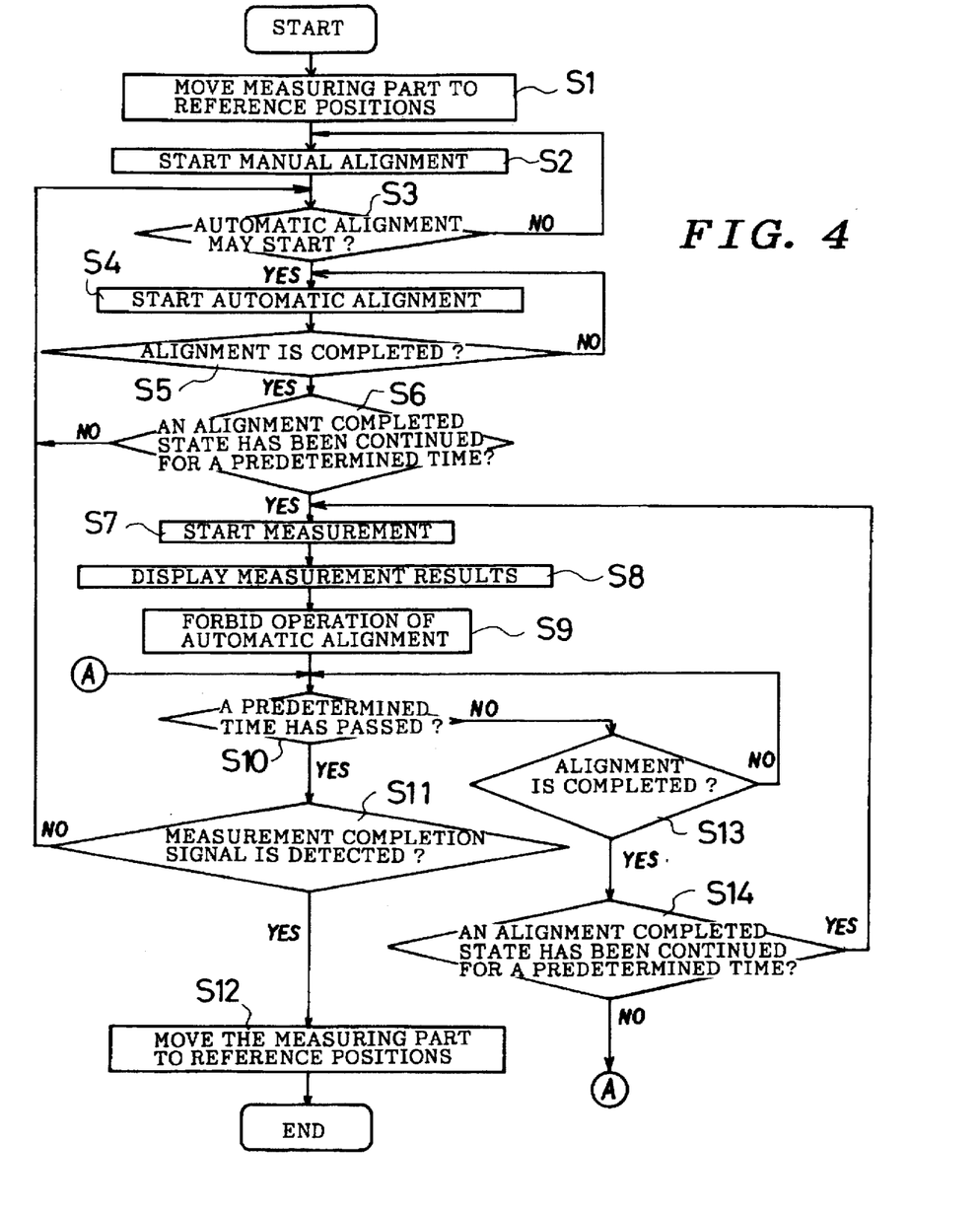
FIG. 4 is a flow chart for explaining the operation of the apparatus in the first embodiment.

Operation of the apparatus constructed above will be described with reference to a flow chart of FIG. 4. In the apparatus a manual alignment mode and an automatic alignment mode can be selected by an alignment mode changing switch. In an automatic alignment mode, an additional mode for stopping automatic alignment operation for a predetermined time every completion of measurement can be selected by a selection switch. The description below adopts a case where an automatic alignment stopping mode is selected.

When the apparatus is supplied with electrical power, the control circuit 62 of the apparatus drives the X- and Z-driving systems 63 and 65 respectively to position the measuring part 4 at a reference position with respect to the main body 3 (S1). A reference position in an X-direction is located in substantially a center point in a movable area of the measuring part 4. The X-driving system 63 moves the measuring part 4 to the reference position by first moving it in one direction until it is detected by the movement limit detecting system 66 and then moving back by the predetermined number of pulses. Memorizing this movement pulse number makes it possible to detect the position of the measuring part 4, so that this information of the position will be used for the moving operation to the reference position after the next time. A reference position in a Z-direction is located in a position nearest to an examiner's side. The movable area of the measuring part 4 in a Y-direction is relatively large and therefore its reference position is not determined in the present embodiment but, of course, it may be determined as well as in the X-direction.

First, the examiner makes the examinee put the head of the examinee on the chin rest 2 and makes positioning adjustment by a movement limit mechanism to determine a limit position in a forward direction in relation to an examinee's eye. This positioning adjustment is described in detail in Japanese Patent Application laid-open No. 5-176895. When a lever for positioning, not illustrated, is depressed down, a microswitch not shown detects it and transmits a detection signal to a control circuit 62. During receiving the detection signal from the microswitch, the control circuit 62 forbids each operation of the X-, Y- and Z-driving systems 63, 64 and 65, and displays messages or marks on the TV monitor 6 to inform of the apparatus being under positioning adjustment.

Next, the examiner performs rough alignment by operating the joy stick 5 in the following manner (S2). The light from the illumination light source 17 is directed to the eye E to illuminate it. And an image of the anterior part of the eye E illuminated is received with the reticle image by the TV camera 16 and displayed on the TV monitor 6. While observing an image of the anterior part and the reticle image displayed on the TV monitor 6, the examiner operates the joy stick 5 and the rotating knob 5a to move the main body 3 forward and backward and to the right and left on the base 1 and the measuring part 4 vertically with respect to the main body 3 so that the circular reticle image is positioned near the center of the iris or pupil of the anterior part image on the TV monitor 6.

When an image of the index i1 is displayed on the TV monitor 6, the two-dimensional position detecting element 37 can detects it, which comes into a state enabling automatic alignment in a right and left, and vertical directions. When the luminous flux of the index i2 is incident on the one-dimensional detecting element 53, automatic alignment in a forward and backward direction may start. At that time, a distance mark (not illustrated in the figure) is displayed on the TV monitor 6.

After completion of rough alignment in the above manner, automatic alignment is performed (S3, S4). In automatic alignment, as mentioned above, the control circuit 62 calculates each displacement amount of the eye E in a vertical, backward and forward, and a right and left directions compared with each proper position on the basis of the signals corresponding to the output of the two-dimensional detecting element 37 and the one-dimensional detecting element 53. Based on these displacement information, the control circuit 62 drives the X-, Y- and Z-driving systems 63, 64 and 65 respectively. When operation of each driving systems 63–65 causes the measuring part 4 to move in each direction with respect to the main body 3, each image of the indexes is simultaneously moved on the two-dimensional detecting element 37 or the one-dimensional detecting element The control circuit 62 judges whether or not a predetermined measurement starting condition is fulfilled, namely, the index images have come into a predetermined permissible area (S5). When it is judged that the index images are within the area, the control circuit 62 outputs signals to stop each of the driving systems, thereby completing automatic alignment (S5:YES). The control circuit 62 also monitors the time during the index images are within the permissible area (S6). When judging that a predetermined time has passed as the measurement condition fulfilled (S6:YES), the control circuit 62 then outputs automatically trigger signals to drive the measuring system to start measurement (S7). The measured results are displayed on the TV monitor 6 (S8).

When measurement is completed, the control circuit 62 drives its timer to forbid automatic alignment operation (S9) for a predetermined time, for example, about 4 seconds. In accordance with the signals from the control circuit 62, each driving system does not operate, not performing alignment. This makes it possible to avoid sequence measurements in a state where an eye to be examined is not fully opened. As described above, the prohibition of automatic alignment in the present embodiment is effected by stopping operation of X-, Y- and Z-driving systems 63, 64 and 65. Alternatively, the automatic alignment may also be forbidden by stopping the projection and the detection itself of index luminous flux to and from the eye to be examined.

During automatic alignment is forbidden, the control circuit 62 drives the character display circuit 70 and the synthesizing circuit 71 to display messages or marks and the like on the TV monitor 6 to inform an examiner so as to make an examinee sufficiently open and fix the eye to be examined. As this information means to instruct the examinee to fully open and fix the eye, sound signals may be substituted for or used with characters displayed on the TV monitor 6.

The control circuit 62, also during automatic alignment is forbidden, judges whether or not the index images are in a permissible area (S10:NO, S13). When it is judged that the index images are within the permissible area (S13:YES), the control circuit 62 monitors its duration (S14) and will generate trigger signals when that state continues for a predetermined time (S14:YES), for example, 1.0 second in the embodiment, thereby making a start of measurement again (S7). Thus, it can be judged that the eye to be examined is fully opened and fixed when the index images are continually in the permissible area. As mentioned above, the monitor of the duration that the index images are in the permissible area is also effected for a period of not forbidding automatic alignment. If setting the duration at the time except the alignment forbidding period (in a sequence measurement mode) so as to be shorter than the duration at the time of forbidding automatic alignment (in a sequence measurement mode), it can realize both rapid measurement and high accurate measurement at the time of a sequence measurement mode. For example, the duration at the time of not forbidding automatic alignment is set to 0.1 second and that at the time of forbidding alignment operation to 1.0 second.

After completion of measurement, when a predetermined time counted by the timer has passed (S10:YES), the control circuit 62 releases forbidding automatic alignment. This release may also be commanded by a signal for changing a right and left eye detected through the right and left eye change detecting means 72 and a signal of a print switch. When the control circuit 62 receives a signal changing a right and left eye to be examined or a measurement completion signal from a print switch and the like (S11:YES), it drives X- and Z-driving systems 63 and 65 to move the measuring part 4 to the reference positions in the X- and Z-directions respectively (S12).

Figure 5:
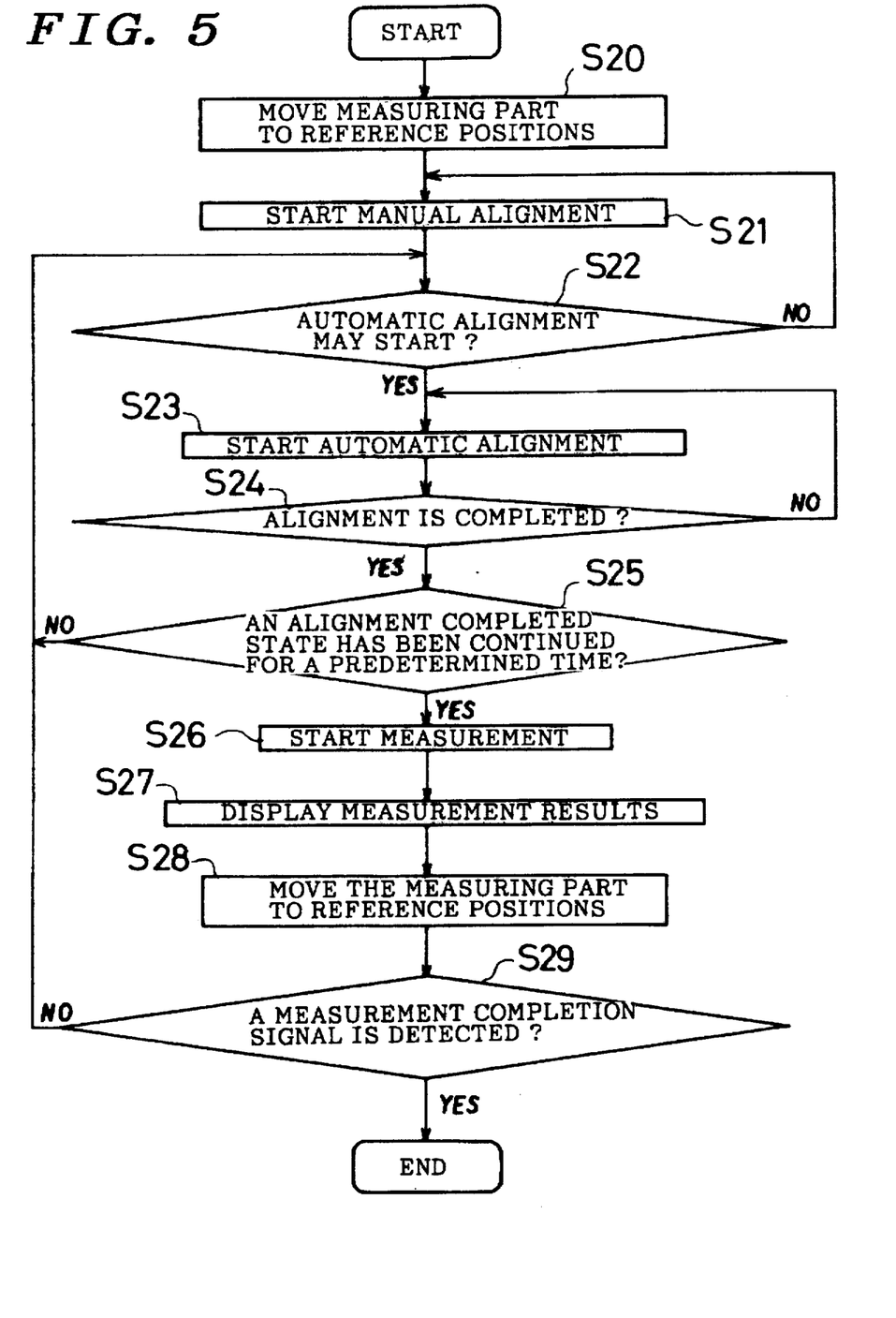
FIG. 5 is a flow chart for explaining the operation of the apparatus in the second embodiment.

FIG. 5 shows a flow chart of operation of the apparatus in the second embodiment. Each element of this embodiment is substantially the same as that of the first embodiment, its explanation will be omitted accordingly.

After completion of rough alignment by manual operation of the examiner (S20, S21), automatic alignment of the apparatus is performed (S22:YES, S23). When a predetermined measurement starting condition is fulfilled by the automatic alignment (S24:YES) and the alignment condition fulfilled state is continued for a predetermined time (S25:YES), measurement is started (S26) and after that, measured results are displayed on the monitor (S27). When the measurement is finished, the control circuit 62 drives the X- and Z-driving systems 63 and 65 to move back the measuring part 4 to the reference positions (S28). This returning operation of the measuring part 4 is effected every the completion of measurement. The reference position in a Z-direction is set in a position nearest to an examiner. Therefore, the measuring part 4 is surely moved in the reference position, which enables the apparatus to once release the alignment completion state. This makes it possible to provide the examinee the time to fully open and fix the eye to be examined prior to the next measurement.

Thereafter, as similar as the above, when the control circuit 62 receives a measurement completion signal (S29: YES), the operation of the second embodiment is finished.

The foregoing description of the preferred embodiment of the invention has been presented for purposes of illustration and description. It is not intended to be exhaustive or to limit the invention to the precise form disclosed, and modifications and variations are possible in light of the above teachings or may be acquired from practice of the invention. The embodiment chosen and described in order to explain the principles of the invention and its practical application to enable one skilled in the art to utilize the invention in various embodiments and with various modifications as are suited to the particular use contemplated. It is intended that the scope of the invention be defined by the claims appended hereto, and their equivalents.

What is claimed is:

1. An ophthalmic apparatus including measuring means for measuring an eye to be examined, the apparatus comprising:

moving means for moving said measuring means with respect to the eye to be examined;

detecting means for detecting an alignment state between said measuring means and the eye to be examined;

control means for controlling operation of said moving means on the basis of detection results of said detecting means;

judging means for judging the alignment state on the basis of the detection results of said detecting means;

trigger signal generating means for generating trigger signals to make said measuring means start measurement based on judgement results of said judging means; and stopping means for stopping operation of said moving means for a first predetermined time after completion of measurement by said measuring means.

2. An ophthalmic apparatus according to claim 1, wherein said judging means includes a first monitoring means for monitoring whether or not a predetermined alignment state between said measuring means and an eye to be examined continues for a second predetermined time during said moving means is stopped operating by said stopping means, and said trigger signal generating means generates trigger signals when said first monitoring means determines that the alignment state has been continued for the second predetermined time.

3. An ophthalmic apparatus according to claim 2, wherein the first predetermined time is longer than the second predetermined time.

4. An ophthalmic apparatus according to claim 3, wherein the first predetermined time is set to 4 seconds and the second predetermined time is set to 1 second.

5. An ophthalmic apparatus according to claim 2, wherein said judging means comprises a second monitoring means for monitoring whether or not, in moving said moving means, the predetermined alignment state continues for a third predetermined time shorter than the second predetermined time, and said trigger signal generating means generates trigger signals when the second monitoring means determines that the alignment state has been continued for the third predetermined time.

6. An ophthalmic apparatus according to claim 1, further comprising information means for informing an examiner of messages helpful to make an examinee sufficiently open and fix the eye.

7. An ophthalmic apparatus according to claim 6, wherein said information means comprises display means or sound means.

8. An ophthalmic apparatus according to claim 1, wherein said stopping means comprises returning means for returning said measuring means to reference positions where the measuring means is initially positioned before alignment between the measuring means and the eye is started by the moving means, every completion of measurement.

* * * * *